United States Patent
Theillez et al.

(10) Patent No.: US 8,486,151 B2
(45) Date of Patent: Jul. 16, 2013

(54) COTYLOID ELEMENT OF A HIP PROSTHESIS, AND TOTAL HIP PROSTHESIS COMPRISING SAME

(76) Inventors: Boris Theillez, Bourg de Peage (FR); Nicolas Chanzy, Boulogne Billancourt (FR); Frederic Farizon, St. Chamond (FR); Philippe Adam, Quatzenheim (FR); Remi Philippot, Saint Etienne (FR); Eric Favre, Chamery (FR); Rodophe Limozin, Rodez (FR); Gilles Provost, Certines (FR); Serge Doycinovich, Bourg en Bresse (FR); Jean-Philippe Camilleri, Lyons (FR)

( * ) Notice: Subject to any disclaimer, the term of this patent is extended or adjusted under 35 U.S.C. 154(b) by 75 days.

(21) Appl. No.: 12/935,117

(22) PCT Filed: Mar. 27, 2009

(86) PCT No.: PCT/FR2009/000341
§ 371 (c)(1),
(2), (4) Date: Jan. 11, 2011

(87) PCT Pub. No.: WO2009/130406
PCT Pub. Date: Oct. 29, 2009

(65) Prior Publication Data
US 2011/0264231 A1    Oct. 27, 2011

(30) Foreign Application Priority Data
Mar. 28, 2008    (FR) .................................. 08 01719

(51) Int. Cl.
*A61F 2/32* (2006.01)

(52) U.S. Cl.
USPC .................... 623/22.31; 623/22.27; 623/22.36

(58) Field of Classification Search
USPC ............................................ 623/22.11–22.39
See application file for complete search history.

(56) References Cited

U.S. PATENT DOCUMENTS

| | | | |
|---|---|---|---|
| 2007/0099153 A1* | 5/2007 | Fromovich | 433/174 |
| 2008/0241791 A1* | 10/2008 | Bulard et al. | 433/174 |
| 2008/0249579 A1* | 10/2008 | Taylor | 606/317 |

* cited by examiner

*Primary Examiner* — Thomas J Sweet
*Assistant Examiner* — Rebecca Preston
(74) *Attorney, Agent, or Firm* — McCarter & English, LLP

(57) ABSTRACT

The invention relates to a cotyloid component of a hip prosthesis, said cotyloid component being hollow and in the form of a cup whose outer part has a thread allowing it to be fixed in the iliac bone, said thread being a discontinuous self-cutting double thread (20, 21), and said cotyloid component having a flattened upper pole (1), a coating that promotes osseointegration on its outer face (10), and a concave, substantially hemispherical and polished inner surface (11), characterized in that: (a) the pitch of the threads (20, 21) decreases from the upper pole (1) towards the equatorial periphery (3) of the cotyloid component, (b) the thicknesses of the threads (20, 21) increase from the upper pole (1) of the cotyloid component towards its periphery (3), (c) the crest of the threads (20, 21) is sharp towards the pole (1) of the cotyloid component and rounded or substantially trapezoidal towards the equatorial periphery (3) of the cotyloid component.

13 Claims, 3 Drawing Sheets

COTYLOID ELEMENT OF A HIP PROSTHESIS, AND TOTAL HIP PROSTHESIS COMPRISING SAME

CROSS-REFERENCE TO RELATED APPLICATIONS

This application is the U.S. National Phase of International Application No. PCT/FR2009/000341, entitled "Cotyloid Element of a Hip Prosthesis, and Total Hip Prosthesis Comprising Same," filed on Mar. 27, 2009, which, in turn, claims priority to French Patent Application No. FR 0801719, filed Mar. 28, 2008, the disclosures of both of which are hereby incorporated by reference in their entireties.

FIELD OF THE INVENTION

The invention relates to hip prostheses, and more specifically to the acetabular elements of hip prostheses intended to be implanted without cement.

PRIOR ART

Hip prostheses are implants commonly used in human surgery to treat fractures of the upper end of the femur, as well as advanced rheumatic conditions of the hip. They can be uniquely femoral, i.e. comprise only one element intended to replace the upper end of the femur and provided at the end with a spherical head intended to be inserted into the patient's acetabular cavity. They can be total, i.e. comprise, in addition to the femoral element, an artificial acetabulum that the surgeon implants in the patient's hip bone, in place of the patient's natural cavity.

In total hip prostheses, the femoral element normally comprises:
 a substantially rectilinear stem anchored in the femur and ending with a conical distal end (neck) for insertion of the spherical head of variable diameter,
 and a spherical head placed at the end of the prosthetic neck.

The acetabular element normally comprises a portion attached in the natural cavity of the hip bone. This portion attached in the bone is provided with a sliding surface having the shape of a hemispherical cavity.

According to the type of prosthesis, the acetabular element can consist of a single part made of metal, ceramic or polyethylene. However, to enable the attachment without cement of the acetabular cup in the hip bone, many models, in particular those referred to as having "dual mobility" consist of the following elements:
 a metal shell, generally in the form of a cap, attached in the bone,
 a polyethylene insert, placed in the shell and in which the spherical prosthetic head of the femoral element is pivotably connected.

The main problems encountered in surgical practice are wear on the surfaces between the femoral head and the acetabular part, associated with stress friction, and the attachment of the metal shell in the bone.

A number of modes of attachment of the metal shell are currently used, in particular sealing (a), impaction (b), expansion (c) and screwing (d), described in detail below.

a) Sealing consists of placing, between the bone and the shell, an acrylic-based polymerizable cement that is anchored in the bone and ensures the primary and secondary attachment of the shell. However, loosening can occur between the bone and the shell more or less over the long term in particular due to properties of the bone and the cement.

b) Impaction consists of inserting the metal shell into the bony acetabulum prepared by hemispherical drills calibrating the bone to a diameter smaller than the diameter of the metal shell. A coating and surface protuberances located at the periphery of the shell improve the primary attachment and increase bone regrowth. This mechanical strength depends on the bone preparation, but also and mainly on the quality of the bone. Many models propose complementary attachments, for example with pins or screws, positioned in holes provided in the metal shell.

This technique has in particular the following disadvantages: micromobility is possible between the screws or the pins, and poor impaction of the pins or screws increases wear.

c) Expansion consists of using a metal shell designed so as to be open in the bone cavity previously prepared as in b). There are two types of expansion shells:
  a. shells provided with petals distributed symmetrically over the periphery of the shell and held by a ring that is removed during insertion of the shell to ensure expansion;
  b. an insert screwed inside the metal shell and of which the screwing ensures expansion.

The expansion shells have in particular the following disadvantages: the plastic insert must absorb all of the stress and not be deformed so as to durably ensure expansion; in the case of the shell provided with petals, slots increase the bone/plastic portion contact due to the creeping phenomenon, which promotes osteolysis.

d) In screwed shells, a metal shell having a threading on its external surface is screwed directly into the hip bone. The external portion of the shell can be covered with materials promoting bone regrowth.

This type of acetabulum is known and described in many prior art documents. For example, patent FR 2 622 432 relates to a screwable acetabulum ring for a hip prosthesis. The ring described in this patent has a frustoconical shape, and is provided with a self-tapping screw thread. Patent application FR 2 639 822 describes a substantially hemispherical acetabulum provided with an external screw thread. In this document, the anchoring of the prosthesis in the bone is facilitated by the presence of tabs that are resiliently deformable so as to be pushed after screwing of the acetabulum into the bone by attached means capable of cooperating with at least one selected tab. U.S. Pat. No. 6,146,425 relates to an acetabulum provided with an external self-tapping screw thread of which the edges have a particular angular orientation and a variable step for facilitated screwing and better anchoring in the hip bone.

Such a device is also known from the French patent FR 2 585 946. This patent describes an acetabular component including a titanium hemispherical cap having, on its external surface, a self-tapping screw thread with an interrupted double thread.

The disadvantages of the screwed acetabula as described in the aforementioned prior art documents are the following: poor positioning during installation increases the rate of dislocation, promotes wear, and adversely affects osteointegration. Moreover, repositioning of the prosthesis is difficult due to the existence of the screw thread.

This invention is intended to overcome these specific disadvantages, so as to provide the following advantages:
 optimal mechanical strength regardless of the bone quality,
 precise and easy positioning,
 reduced wear at the joint, the possibility of placing a mobile polyethylene insert or a metal pivoting head with a large diameter directly in the shell.

Subject Matter of the Invention

The invention first relates to an acetabular component of a hip prosthesis, in which said acetabular component is hollow and has a shell shape, of which the external portion has a screw thread for enabling said acetabular component to be attached in the acetabular cavity of the suitably prepared hip bone, said screw thread comprising an interrupted self-tapping double thread (20, 21), said acetabular component being provided with a cleared upper pole (1), said acetabular component being provided on its external face (10) with a osteointegration-promoting coating (typically a porous titanium coating associated with a calcium hydroxyapatite coating), said acetabular component being provided with a substantially hemispherical concave polished internal surface (11), and said acetabular component being characterized in that:

the pitch of the screw threads (20, 21) decreases from the upper pole (1) to the equatorial periphery (3) of the acetabular component, the thicknesses of the threads (20, 21) increase from the upper pole (1) of the acetabular component to the periphery (3) thereof, the edge of the threads (20, 21) is cutting on the side of the pole (1) of the acetabular component and rounded or substantially trapezoidal on the side of the equatorial periphery (3) of the acetabular component, and the profile of said edge varies continuously and regularly from the pole (1) to the equatorial periphery (3).

Advantageously, the osteointegration-promoting coating is absent over a crown of height h of between 2 and 5 mm on the equatorial periphery of the acetabulum, and preferably over a height h of between 3 and 4 mm.

This invention also relates to a plate enabling the positioning by screwing and removal by unscrewing of the acetabulum according to the invention in the hip bone by gripping by means of screwing/unscrewing notches (4), characterized in that the plate comprises protuberances (9) intended to cooperate with the notches (4) of said acetabular component so as to enable the acetabular component to be gripped and screwed or unscrewed.

The invention finally relates to a total hip prosthesis including a acetabular component according to the invention.

LIST OF REFERENCES

Figure 1A:
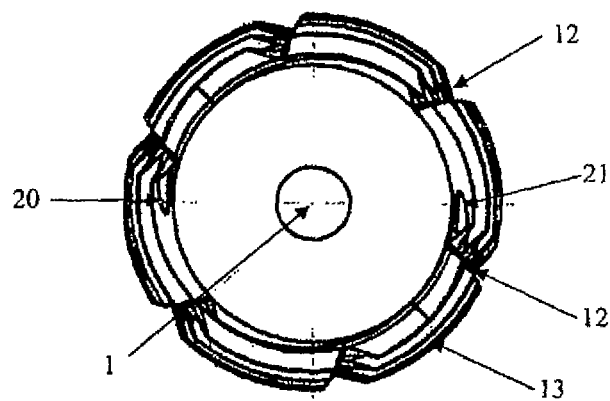
FIGS. 1*a*, 1*b* and 1*c* respectively show a top view, a side view and a transverse cross-section of an acetabulum according to the invention.

1. Upper pole
20, 21. Double screw thread
3. Equatorial periphery of the acetabular component
4. Screwing and unscrewing notches
5. Height h without osteointegration-promoting coating
6, 61, 62. Thread portions located near the upper pole
7, 71, 72. Thread portions located near the equatorial periphery
8. Bearing face of the plate
9. Protuberances
10. External face of the acetabulum
11. Internal face of the acetabulum
12. Interruption of the screw thread.

DESCRIPTION OF THE INVENTION

The invention first relates to an artificial hollow acetabular element (also called acetabulum) in the form of a shell.

The acetabulum according to the invention is preferably made of metal or a metal alloy such as stellites (chromium-cobalt alloys) or stainless steel.

The external portion of the acetabulum according to the invention comprises a screw thread enabling it to be attached in the hip bone. This screw thread is self-tapping.

Figure 1B:
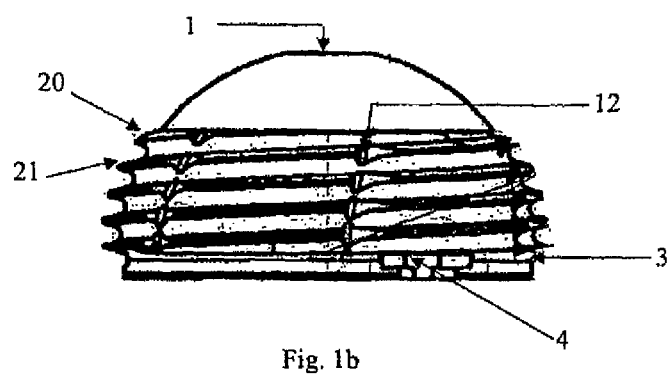
Figure 1C:
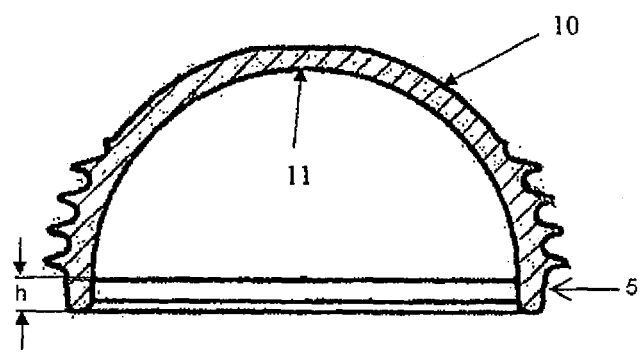

The screw thread of the acetabulum according to the invention is a screw thread with a double thread 20, 21, as shown in FIGS. 1*a*, 1*b* and 1*c*. The main advantage of such a screw thread with a double thread 20, 21 is that it enables the screw thread pitch to be increased, and therefore the number screwing turns is less than the usual number needed for screwed acetabula of the prior art, thereby enabling quick attachment of the acetabulum in the bone. The acetabulum according to the invention also enables precise attachment of the acetabulum in the bone, owing to the fact that the double screw thread has threads 20, 21 beginning at 180° from one another on pole of the acetabulum as shown in FIG. 1*a*, thereby facilitating the precise positioning of the acetabulum at the beginning of the screwing.

The threads 20, 21 are interrupted by non-threaded portions 12, so that bone can be removed during tapping caused by positioning of the acetabulum, and so that the bone is again attacked by a cutting edge of the screw thread. There are advantageously 6 non-threaded portions 12, regularly spaced apart over the periphery of the acetabulum as shown in FIGS. 1*a* and 1*b*. There may, however, be more or fewer without changing the scope of the invention. Advantageously, the non-threaded portions correspond to more than 25% of the screw thread, measured over the external diameter of the screw thread.

Figures 2, 2A, 2B:
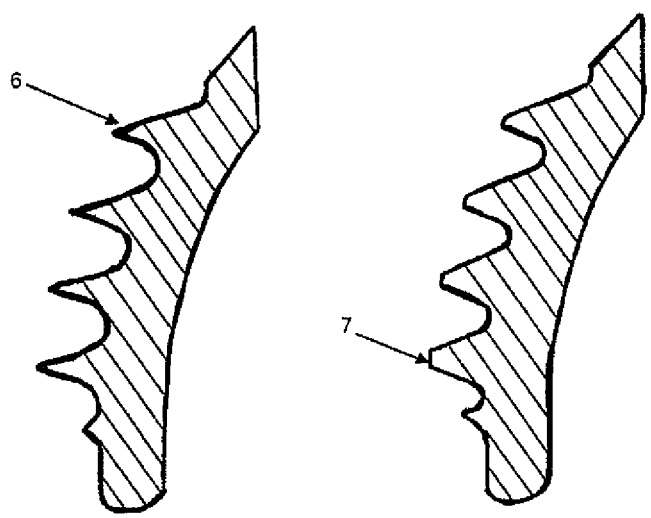
FIG. 2 shows an enlarged cross-section view of the screw thread of the acetabulum according to the invention.
FIG. 2*a* shows an enlarged cross-section view of the portion first coming into contact with the bone in the direction of screwing.
FIG. 2*b* shows an enlarged cross-section view of the portion last coming into contact with the bone in the direction of screwing.
Figure 3A:
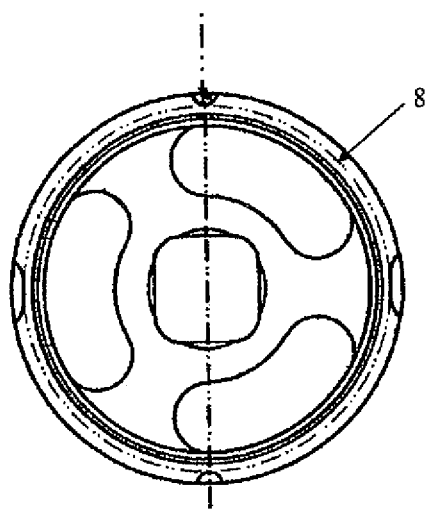
FIGS. 3*a*, 3*b*, 3*c* and 3*d* respectively show a front view, a cross-section view according to line AA, a bottom view and a side view of a plate for holding the acetabulum according to the invention.
Figure 3B:
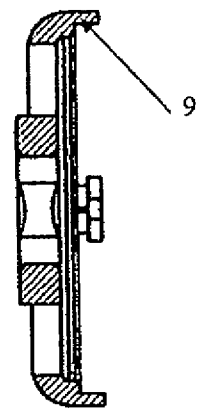
Figure 3C:
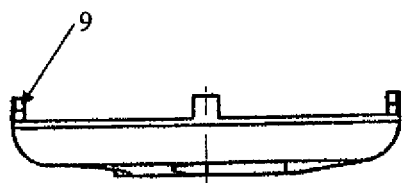
Figure 3D:
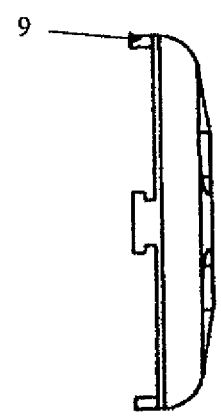

The threads do not have a constant thickness, but have a thickness that increases in the direction of the screwing, from the upper pole 1 to the equatorial periphery 3 of the acetabulum. In addition, as shown in FIG. 2, the thread portions 6 located near the upper pole 1 have sharp substantially triangular cutting edges, and the thread portions 7 located near the equatorial periphery 3 have edges with a rounded or trapezoidal cross-section. The thickness of the threads also increases in the direction of screwing in each of the threaded portions 13 located between the non-threaded portions 12, as shown in FIGS. 2*a* and 2*b*. FIG. 2*a* shows an enlarged cross-section view of the portion first coming into contact with the bone in the direction of screwing. FIG. 2*b* shows an enlarged cross-section view of the portion last coming into contact with the bone in the direction of screwing.

The fact of having a thin thread with a sharp cutting edge on the side of the pole 1, i.e. on the portion of the screw thread that comes into contact with the bone at the beginning of the screwing of the acetabulum, and also a more cutting portion on the side of each threaded portion 13 first coming into contact with the bone in the direction of screwing, enables effective self-tapping of the bone by the acetabulum according to the invention. The fact of having a thread with a thicker edge on the side of the equator, i.e. at the end of screwing, and also a less cutting portion on the side of each threaded portion 13 last coming into contact with the bone in the direction of screwing, enables better attachment of the acetabulum according to the invention in the bone because, in this way, the threads have a large surface in contact with the bone, and the less cutting shape of the threads produces less mechanical stress in the bone.

The pitch of the screw threads 20, 21 decreases from the upper pole 1 to the equatorial periphery 3 of the acetabular component. The pitch of the threads 20, 21 is between 2 and 5 mm, and preferably between 3 and 4 mm.

The acetabulum according to the invention, generally with an approximately hemispherical shape, is further provided with a cleared upper pole 1, shown in FIGS. 1a, 1b and 1c, so as to prevent problems of hyperpressure in the positioning of the acetabulum in the acetabular cavity of the hip bone.

The acetabulum according to the invention is further provided on its external face 10 with an osteointegration-promoting coating, such as a porous titanium coating associated with a calcium hydroxyapatite coating (not shown). Indeed, calcium hydroxyapatite is a mineral component of the bone that can be chemically produced. The adjacent bone identifies hydroxyapatite as one of its constituents and quickly grows on the coating of the prosthesis, thus ensuring good attachment of the acetabulum in the bone. The role of the titanium is, on the one hand, to form a barrier to the hydroxyapatite, which, without it, would tend to spread into the metal forming the acetabulum, and, on the other hand, to create micro-reliefs ensuring the bony surface anchoring. The calcium hydroxyapatite coating can be obtained by plasma spraying or any other suitable technique known to a person skilled in the art. Similarly, the titanium coating can be obtained by any technique known to a person skilled in the art, such as, for example, plasma spraying, or vapor deposition.

In a strongly preferred embodiment of the acetabular component according to the invention, the osteointegration-promoting coating, such as a titanium and calcium hydroxyapatite coating, is absent over a crown 5 of height h on the equatorial periphery 3 of the acetabulum, so as to prevent a release of material that may cause possible wear by forming a third body in the friction areas. The height h is between 2 and 5 mm, and preferably between 3 and 4 mm.

Finally, the concave internal surface 11 of the acetabulum according to the invention is substantially hemispherical and has a mirror-type polish, obtained by any technique known to a person skilled in the art.

The acetabulum according to the invention can receive either a prosthetic head with a diameter equal to the internal diameter of the shell, or, preferably, a mobile insert, that can be comprised of any material capable of limiting the friction coefficient of the head on the acetabulum and capable of resisting wear, this material preferably being polyethylene. This mobile insert is preferably a substantially hemispherical shell with an external diameter equal to the internal diameter of the shell and an internal diameter equal to that of the prosthetic head received by said insert.

The attachment of the acetabulum according to the invention in the patient's hip bone is performed by means of a plate that enables easy and precise screwing and unscrewing of the acetabulum. The plate is shown in FIG. 3. In addition, screwing and unscrewing notches 4 are present at the periphery of the acetabulum according to the invention, as shown in FIG. 1.

The plate enables the gripping and positioning of the acetabulum in the hip bone. It includes a surface 8 for engagement against the edge of the acetabulum; it also includes projections 9 intended to be engaged and locked in the screwing and unscrewing notches 4 of the acetabulum, so as to enable good gripping of the acetabulum by the plate and effective tightening by screwing or loosening by unscrewing of said acetabulum by means of the plate.

The acetabulum according to the invention is preferably used in association with a femoral element normally comprising a substantially rectilinear stem anchored in the femur and ending with a conical distal end for insertion of the spherical head of variable diameter, and a spherical head placed at the end of the prosthetic neck.

The invention claimed is:

1. A acetabular component of a hip prosthesis comprising: a hollow substantially shell-shaped body defining an upper pole having a planar surface and an opposing equatorial periphery, a substantially hemispherical concave polished internal surface, and an external face defining a screw threaded external portion adapted to attach in an acetabular cavity of a suitably prepared hip bone, said external face having an osteointegration-promoting coating thereon, and said screw threaded external portion including interrupted self-tapping double threads, wherein said threads define an increasing thickness and a decreasing pitch in a direction from the upper pole toward the equatorial periphery, and said threads define an edge progressively changing from a substantially sharp cutting edge to a substantially rounded or trapezoidal edge in said direction.

2. An acetabular component according to claim 1, wherein said osteointegration-promoting coating is a porous titanium coating associated with a calcium hydroxyapatite coating.

3. An acetabular component according to claim 1, further comprising a crown without an osteointegration-promoting coating located at the equatorial periphery and defining a height between 2 mm and 5 mm.

4. An acetabular component according to claim 3, wherein the height of the crown is between 3 mm and 4 mm.

5. An acetabular component according to claim 1, wherein the acetabular component is made of a metal alloy.

6. An acetabular component according to claim 5, wherein the metal alloy is cobalt chromium or stainless steel.

7. An acetabular component according to claim 1, wherein the pitch of the threads varies between 2 mm and 5 mm.

8. An acetabular component according to claim 7, wherein the pitch of the threads varies between 3 mm and 4 mm.

9. An acetabular component according to claim 1, further comprising screwing and unscrewing notches located at the equatorial periphery for the screwing and unscrewing of said acetabular component in the hip bone via a plate.

10. An acetabular component according to claim 9 in combination with a plate for engaging said screwing and unscrewing notches to at least one of screw the acetabular component into the hip bone and unscrew the acetabular component therefrom, wherein said plate comprises projections adapted to cooperate with said notches of said acetabular component to grip and screw or unscrew the acetabular component.

11. An acetabular component according to claim 1, further comprising a mobile insert receivable within said hollow substantially shell-shaped body of the acetabular component and adapted to resist wear and limit friction between the acetabular component and a hip bone head or hip bone prosthesis head.

12. An acetabular component according to claim 11, wherein said mobile insert is made of polyethylene.

13. An acetabular component according to claim 1, wherein said acetabular component comprises at least a portion of a total hip prosthesis.

* * * * *